(12) United States Patent
Riley

(10) Patent No.: US 8,126,657 B2
(45) Date of Patent: Feb. 28, 2012

(54) METHOD AND APPARATUS FOR THE CALCULATION OF COAL ASH FUSION VALUES

(75) Inventor: John T. Riley, Bowling Green, KY (US)

(73) Assignee: Leco Corporation, St. Joseph, MI (US)

( * ) Notice: Subject to any disclaimer, the term of this patent is extended or adjusted under 35 U.S.C. 154(b) by 0 days.

(21) Appl. No.: 12/938,543

(22) Filed: Nov. 3, 2010

(65) Prior Publication Data

US 2011/0071788 A1 Mar. 24, 2011

Related U.S. Application Data

(62) Division of application No. 11/937,566, filed on Nov. 9, 2007, now Pat. No. 7,885,772.

(51) Int. Cl.
*G06F 17/18* (2006.01)
(52) U.S. Cl. .......................................... 702/31
(58) Field of Classification Search ...................... 702/31
See application file for complete search history.

(56) References Cited

U.S. PATENT DOCUMENTS

| | | | |
|---|---|---|---|
| 4,462,963 | A | 7/1984 | O'Brien et al. |
| 4,522,787 | A | 6/1985 | O'Brien et al. |
| 2009/0284804 | A1* | 11/2009 | Matsuda et al. ............. 358/448 |

OTHER PUBLICATIONS

"Standard Test Method for Fusibility of Coal and Coke Ash" Method D1857-87, American Society for Testing and Materials, Philadelphia, PA: The Society, (Reapproved 2000).

Lloyd et al. "Estimation of Ash Fusion Temperatures from Elemental Composition: A Strategy for Regressor Selection", 201$^{st}$ Amer. Chemical Society Mtg, Div. of Fuel Chemistry, vol. 36, No. 1, Apr. 14-19, 1991, p. 235-249.
Lloyd et al. "Estimation of Ash Fusion Temperatures", Journal of Coal Quality Jan.-Mar. 1993, vol. 12, No. 1, p. 30-36.
Lloyd et al. "Ash Fusion Temperatures under Oxidizing Conditions", Energy & Fuels, 1993, 7, p. 490-494.
"Methods for Analysis and Testing of Coal and Coke—Part 113: Determination of Ash Fusibility" British Standard BS 1016-113 (1995).
"Coal and Coke—Analysis and Testing Part 15: Higher rank Coal Ash and Coke Ash-Ash Fusibility" Standards Association of Australia, AS 1038.15, 1995.
"Solid mineral fuels—Determination of fusibility of ash—High-temperature tube method" International Organization for Standardization, ISO 540 Third Edition Mar. 15, 1995.
"Determination of Fusibility of Fuel Ash" DIN 51730, Deutsches Institut fur Normung, Apr. 1998.
Seggiana et al. "Prediction of Coal Ash Thermal Properties Using Partial Least-Squares Regression" Ind. Eng. Chem. Res. 2003, 42, p. 4919-4926.
M. Seggiani, "Empirical correlations of the ash fusion temperatures and temperature of critical viscosity for coal and biomass ashes" 1999 Elsevier Science Ltd , pp. 1121-1125.

* cited by examiner

*Primary Examiner* — Tung S Lau
(74) *Attorney, Agent, or Firm* — Price Heneveld LLP

(57) ABSTRACT

The IT and FT values for coal and coke samples can be accurately predicted by applying equations to determined ST and HT temperatures. For reducing atmospheres, the equations are $IT=C_1 \times ST - C_2 \times HT + C_3$ and $FT=C_4 \times HT - C_5 \times ST + C_6$. For oxidizing atmospheres, the equations are $IT=C_7 \times ST - C_8 \times HT + C_9$ and $FT=C_{10} \times HT - C_{11} \times ST + C_{12}$. IT is the initial deformation temperature. ST is the softening temperature. HT is the hemispherical temperature. FT is the fluid temperature. $C_1$-$C_{12}$ are constants determined by multi-linear regression coefficient analytical techniques on a collection of data.

18 Claims, 4 Drawing Sheets

FIG. 2

Ash Fusion Calculations -- Reducing

| Coal | IT | ST | HT | FT | Calc IT | Error | Square Error | Calc FT | Error | Square Error |
|---|---|---|---|---|---|---|---|---|---|---|
| 1997-4 | 1207.44 | 1290.98 | 1339.09 | 1386.53 | 1240.08 | 32.64 | 1065.56 | 1401.565 | 15.04 | 226.09 |
| 1998-1 | 1383.22 | 1431.26 | 1474.73 | 1509.62 | 1368.63 | -14.59 | 212.88 | 1521.597 | 11.97 | 143.36 |
| 1998-2 | 1152.76 | 1163.55 | 1175.27 | 1197.30 | 1150.44 | -2.33 | 5.41 | 1216.436 | 19.14 | 366.26 |
| 1998-3 | 1249.35 | 1296.41 | 1332.78 | 1361.57 | 1252.78 | 3.42 | 11.72 | 1384.553 | 22.98 | 528.10 |
| 1998-4 | 1199.34 | 1235.02 | 1263.14 | 1322.66 | 1203.39 | 4.04 | 16.34 | 1312.758 | -9.91 | 98.12 |
| 1999-1 | 1137.61 | 1152.95 | 1168.23 | 1212.53 | 1138.59 | 0.97 | 0.95 | 1213.365 | 0.84 | 0.70 |
| 1999-2 | 1243.36 | 1283.77 | 1329.05 | 1405.87 | 1235.51 | -7.85 | 61.61 | 1389.652 | -16.22 | 263.14 |
| 1999-3 | 1176.81 | 1192.63 | 1203.85 | 1243.67 | 1176.78 | -0.03 | 0.00 | 1242.172 | -1.50 | 2.25 |
| 1999-4 | 1170.12 | 1195.89 | 1214.55 | 1244.13 | 1174.72 | 4.60 | 21.20 | 1259.118 | 14.99 | 224.77 |
| 2000-1 | 1104.23 | 1146.91 | 1174.90 | 1225.45 | 1124.68 | 20.45 | 418.25 | 1231.654 | 6.20 | 38.44 |
| 2000-2 | 1377.14 | 1431.69 | 1461.12 | 1486.67 | 1378.40 | 1.26 | 1.59 | 1495.667 | 9.00 | 80.97 |
| 2000-3 | 1154.30 | 1170.38 | 1186.03 | 1218.21 | 1153.92 | -0.38 | 0.15 | 1230.066 | 11.85 | 140.54 |
| 2000-4 | 1262.44 | 1281.57 | 1307.59 | 1374.44 | 1246.43 | -16.01 | 256.43 | 1351.531 | -22.91 | 524.91 |
| 2001-1 | 1107.02 | 1122.75 | 1144.26 | 1218.54 | 1107.40 | 0.38 | 0.14 | 1197.353 | -21.19 | 448.88 |
| 2001-2 | 1223.92 | 1252.94 | 1282.67 | 1341.82 | 1218.34 | -5.58 | 31.10 | 1332.211 | -9.61 | 92.41 |
| 2001-3 | 1124.95 | 1148.10 | 1190.70 | 1250.74 | 1115.98 | -8.97 | 80.49 | 1260.127 | 9.39 | 88.18 |
| 2001-4 | 1208.40 | 1224.43 | 1233.54 | 1255.48 | 1206.63 | -1.77 | 3.15 | 1267.399 | 11.92 | 142.13 |
| 2002-1 | 1127.10 | 1164.17 | 1207.44 | 1265.47 | 1129.90 | 2.80 | 7.83 | 1276.141 | 10.67 | 113.91 |
| 2002-2 | 1214.10 | 1229.56 | 1244.86 | 1307.51 | 1207.07 | -7.03 | 49.46 | 1283.719 | -23.79 | 565.90 |
| 2002-3 | 1245.26 | 1264.66 | 1284.48 | 1340.04 | 1235.45 | -9.81 | 96.27 | 1324.385 | -15.65 | 245.05 |
| 2002-4 | 1120.70 | 1164.68 | 1229.99 | 1285.92 | 1115.64 | -5.06 | 25.63 | 1317.913 | 32.00 | 1023.72 |
| 2003-1 | 1280.33 | 1298.36 | 1314.62 | 1360.06 | 1267.96 | -12.37 | 153.11 | 1348.648 | -11.41 | 130.18 |
| 2003-2 | 1324.64 | 1348.02 | 1362.74 | 1412.96 | 1313.40 | -11.24 | 126.40 | 1391.328 | -21.63 | 468.05 |
| 2003-3 | 1192.61 | 1246.41 | 1285.76 | 1350.55 | 1206.08 | 13.47 | 181.32 | 1344.246 | -6.31 | 39.80 |
| 2003-4 | 1326.96 | 1372.63 | 1415.49 | 1469.19 | 1316.61 | -10.35 | 107.17 | 1466.645 | -2.54 | 6.47 |
| 2004-1 | 1416.75 | 1481.653 | 1502.17 | 1514.56 | 1429.04 | 12.29 | 151.06 | 1524.807 | 10.24 | 104.94 |
| 2004-3 | 1105.30 | 1121.47 | 1138.26 | 1189.36 | 1109.41 | 4.11 | 16.90 | 1187.315 | -2.05 | 4.19 |
| 2004-4 | 1178.93 | 1234.18 | 1301.22 | 1418.92 | 1176.63 | -2.30 | 5.28 | 1384.932 | -33.98 | 1154.88 |
| 2005-1 | 1362.06 | 1438.85 | 1459.61 | 1484.98 | 1390.59 | 28.54 | 814.43 | 1485.99 | 1.01 | 1.01 |
| 2005-2 | 1155.16 | 1172.76 | 1189.72 | 1230.683 | 1155.17 | 0.02 | 0.00 | 1234.695 | 4.01 | 16.09 |
| 2005-3 | 1109.84 | 1133.33 | 1155.42 | 1220.78 | 1116.48 | 6.64 | 44.12 | 1208.133 | -12.64 | 159.84 |
| 2005-4 | 1242.64 | 1257.07 | 1268.42 | 1288.31 | 1234.32 | -8.32 | 69.20 | 1301.553 | 13.24 | 175.43 |
| 2006-1 | 1203.01 | 1221.58 | 1231.55 | 1249.46 | 1203.49 | 0.49 | 0.24 | 1266.408 | 16.95 | 287.23 |
| 2006-2 | 1180.40 | 1219.69 | 1262.36 | 1336.51 | 1179.96 | -0.44 | 0.19 | 1325.954 | -10.56 | 111.47 |
| 2006-3 | 1296.42 | 1339.95 | 1386.01 | 1440.75 | 1285.24 | -11.18 | 124.97 | 1442.664 | 1.92 | 3.67 |
| | | | | | 117.7088 | | RMS Error | 126.7877 | | RMS Error |
| | | | | | 1.5627 | | 10.9 | -0.9568 | | 15.1 |
| | | | | | -0.6684 | | | 1.8744 | | |

$$IT\_red\_coeff = \begin{pmatrix} 117.7088 \\ 1.5627 \\ -0.6684 \end{pmatrix}$$

$$FT\_red\_coeff = \begin{pmatrix} 126.7877 \\ -0.9568 \\ 1.8744 \end{pmatrix}$$

| Ash Fusion Calculations -- Oxidizing | | | | | | | | | | | |
|---|---|---|---|---|---|---|---|---|---|---|---|
| Coal | IT | ST | HT | FT | Calc IT | Error | Square Error | | Calc FT | Error | Square Error |
| 1997-4 | 1398.22 | 1428.16 | 1447.20 | 1466.35 | 1393.47 | -4.75 | 22.55 | | 1469.377 | 3.02 | 9.13 |
| 1998-1 | 1483.46 | 1501.39 | 1517.77 | 1524.94 | 1463.04 | -20.42 | 417.16 | | 1531.859 | 6.92 | 47.82 |
| 1998-2 | 1202.71 | 1214.28 | 1224.33 | 1242.42 | 1199.87 | -2.83 | 8.03 | | 1256.505 | 14.08 | 198.39 |
| 1998-3 | 1200.49 | 1255.81 | 1277.73 | 1299.71 | 1231.68 | 31.19 | 972.96 | | 1316.186 | 16.48 | 271.43 |
| 1998-4 | 1262.85 | 1290.78 | 1318.59 | 1366.41 | 1260.80 | -2.05 | 4.22 | | 1359.003 | -7.41 | 54.91 |
| 1999-1 | 1169.47 | 1184.75 | 1203.07 | 1246.12 | 1167.71 | -1.76 | 3.08 | | 1244.341 | -1.78 | 3.16 |
| 1999-2 | 1271.31 | 1309.35 | 1351.75 | 1424.14 | 1269.70 | -1.61 | 2.58 | | 1402.534 | -21.60 | 466.65 |
| 1999-3 | 1191.59 | 1205.76 | 1216.67 | 1262.79 | 1191.48 | -0.11 | 0.01 | | 1250.223 | -12.57 | 157.97 |
| 1999-4 | 1237.29 | 1290.38 | 1311.52 | 1334.98 | 1264.25 | 26.95 | 726.50 | | 1346.547 | 11.57 | 133.77 |
| 2000-1 | 1239.48 | 1273.97 | 1307.38 | 1343.22 | 1241.97 | 2.49 | 6.21 | | 1353.71 | 10.49 | 110.01 |
| 2000-2 | 1449.95 | 1483.30 | 1490.36 | 1511.41 | 1451.56 | 1.61 | 2.60 | | 1498.338 | -13.07 | 170.93 |
| 2000-3 | 1165.50 | 1181.04 | 1200.53 | 1239.26 | 1163.59 | -1.91 | 3.65 | | 1243.062 | 3.80 | 14.46 |
| 2000-4 | 1268.01 | 1285.54 | 1317.41 | 1381.39 | 1253.61 | -14.40 | 207.33 | | 1361.557 | -19.83 | 393.17 |
| 2001-1 | 1124.58 | 1140.55 | 1170.83 | 1233.65 | 1119.80 | -4.78 | 22.81 | | 1225.395 | -8.26 | 68.17 |
| 2001-2 | 1246.79 | 1276.31 | 1307.10 | 1354.68 | 1245.65 | -1.14 | 1.30 | | 1351.11 | -3.57 | 12.73 |
| 2001-3 | 1273.08 | 1315.67 | 1348.93 | 1378.46 | 1280.80 | 7.73 | 59.70 | | 1391.769 | 13.31 | 177.22 |
| 2001-4 | 1234.94 | 1251.47 | 1263.69 | 1283.90 | 1233.20 | -1.74 | 3.04 | | 1294.6 | 10.70 | 114.60 |
| 2002-1 | 1200.52 | 1228.68 | 1267.16 | 1310.54 | 1196.99 | -3.52 | 12.40 | | 1321.277 | 10.74 | 115.26 |
| 2002-2 | 1242.59 | 1256.90 | 1274.36 | 1322.86 | 1235.24 | -7.34 | 53.93 | | 1309.102 | -13.76 | 189.33 |
| 2002-3 | 1271.42 | 1294.97 | 1329.09 | 1359.60 | 1261.09 | -10.33 | 106.69 | | 1374.288 | 14.69 | 215.79 |
| 2002-4 | 1294.88 | 1327.33 | 1352.20 | 1384.13 | 1296.44 | 1.56 | 2.43 | | 1387.269 | 3.14 | 9.86 |
| 2003-1 | 1315.05 | 1327.02 | 1341.97 | 1375.89 | 1301.84 | -13.21 | 174.59 | | 1368.991 | -6.90 | 47.55 |
| 2003-2 | 1335.52 | 1356.09 | 1374.96 | 1412.29 | 1326.60 | -8.92 | 79.54 | | 1402.82 | -9.47 | 89.66 |
| 2003-3 | 1346.17 | 1386.24 | 1400.74 | 1423.79 | 1357.12 | 10.95 | 119.99 | | 1422.611 | -1.18 | 1.40 |
| 2003-4 | 1385.18 | 1431.38 | 1461.88 | 1487.17 | 1389.90 | 4.73 | 22.35 | | 1493.112 | 5.94 | 35.30 |
| 2004-1 | 1490.72 | 1505.164 | 1511.49 | 1522.77 | 1472.30 | -18.42 | 339.27 | | 1517.086 | -5.68 | 32.30 |
| 2004-2 | 1309.15 | 1357.26 | 1411.86 | 1464.21 | 1307.23 | -1.92 | 3.67 | | 1468.687 | 4.47 | 20.02 |
| 2004-3 | 1203.23 | 1226.42 | 1243.10 | 1284.33 | 1207.36 | 4.14 | 17.10 | | 1279.667 | -4.66 | 21.73 |
| 2004-4 | 1245.46 | 1301.53 | 1367.35 | 1438.94 | 1249.02 | 3.56 | 12.67 | | 1437.805 | -1.14 | 1.30 |
| 2005-1 | 1429.66 | 1489.02 | 1497.86 | 1502.435 | 1455.85 | 26.19 | 686.14 | | 1506.82 | 4.39 | 19.23 |
| 2005-2 | 1165.15 | 1181.79 | 1202.37 | 1249.06 | 1163.66 | -1.49 | 2.23 | | 1245.727 | -3.33 | 11.08 |
| 2005-3 | 1135.58 | 1153.36 | 1183.01 | 1247.30 | 1132.05 | -3.53 | 12.43 | | 1236.036 | -11.26 | 126.88 |
| 2005-4 | 1249.12 | 1264.09 | 1277.97 | 1300.04 | 1243.97 | -5.15 | 26.48 | | 1309.214 | 9.18 | 84.22 |
| 2006-1 | 1211.99 | 1229.01 | 1240.87 | 1266.48 | 1212.53 | 0.54 | 0.29 | | 1273.321 | 6.84 | 46.75 |
| 2006-2 | 1351.72 | 1377.92 | 1396.69 | 1427.58 | 1346.95 | -4.77 | 22.73 | | 1422.695 | -4.88 | 23.84 |
| 2006-3 | 1378.47 | 1427.43 | 1449.40 | 1475.28 | 1391.12 | 12.65 | 160.14 | | 1474.003 | -1.28 | 1.64 |
| | | | | | | | RMS Error | | | | RMS Error |
| | | | | | 77.3248 | | 11.0 | | 122.228 | | 9.9 |
| | | | | | 1.5016 | | | | -0.894 | | |
| | | | | | -0.5724 | | | | 1.8131 | | |

$$IT\_oxy\_coeff = \begin{pmatrix} 77.3248 \\ 1.5016 \\ -0.5724 \end{pmatrix}$$

$$FT\_oxy\_coeff = \begin{pmatrix} 122.2880 \\ -0.8940 \\ 1.8131 \end{pmatrix}$$

FIG. 3

For reducing atmospheres:
$$IT = C_1 \times ST - C_2 \times HT + C_3$$
$$FT = C_4 \times HT - C_5 \times ST + C_6$$
For oxidizing atmospheres:
$$IT = C_7 \times ST - C_8 \times HT + C_9$$
$$FT = C_{10} \times HT - C_{11} \times ST + C_{12}$$

Where: IT is the initial deformation temperature;
ST is the softening temperature;
HT is the hemispherical temperature;
FT is the fluid temperature; and
$C_1$-$C_{12}$ are constants determined by multi-linear regression coefficient analytical techniques on the collection of data, where (all temperatures in °C):

| | | | |
|---|---|---|---|
| $C_1 = 1.5627$ | $C_4 = 1.8744$ | $C_7 = 1.5016$ | $C_{10} = 1.8131$ |
| $C_2 = 0.6684$ | $C_5 = 0.9568$ | $C_8 = 0.5724$ | $C_{11} = 0.8940$ |
| $C_3 = 117.7088$ | $C_6 = 126.7877$ | $C_9 = 77.3248$ | $C_{12} = 122.2880$ |

When Fahrenheit degrees are employed, $C_3 = 215.259$; $C_6 = 230.856$; $C_9 = 130.665$; and $C_{12} = 223.750$. All other constants remain the same.

FIG. 4

METHOD AND APPARATUS FOR THE CALCULATION OF COAL ASH FUSION VALUES

CROSS-REFERENCE TO RELATED APPLICATIONS

This application is a divisional of U.S. patent application Ser. No. 11/937,566, filed on Nov. 9, 2007, entitled METHOD AND APPARATUS FOR THE CALCULATION OF COAL ASH FUSION VALUES, now U.S. Pat. No. 7,885,772, the entire disclosure of which is incorporated herein by reference.

BACKGROUND OF THE INVENTION

The present invention is a method and apparatus for the calculation of coal ash fusion values based upon the measurement of predetermined ash fusion values.

The efficient operation of coal-fired power plant boilers and other boilers and furnaces with a minimum of slagging and fouling problems depends on the determination of accurate ash fusion temperatures for the coals used as fuels. Such industrial combustion equipment may remove the byproducts of the combustion process in either a solid or liquid form depending on equipment type. It is imperative that the coal utilized maintain appropriate ash properties during the entire handling process. Ash fusion temperatures are a useful guide to a coal's expected behavior.

Before coal or coke is burned in a furnace, the fuel is analyzed to determine the fusibility of the coal or coke ash. Burning coal or coke in a commercial steel mill furnace, which generates temperatures sufficiently high to fuse the ash, causes the ash to collect on various furnace components, most notably the furnace grates. If collection becomes excessive, the furnace must be shut down, cooled, and cleaned, requiring costly excessive periods of furnace inactivity. By selecting coal with desired properties, such problems can be minimized.

The ASTM standard test method for determining the fusibility of coal and coke ash requires the prepared ash to be formed into triangular, generally pyramid-shaped cones which are placed within an analytical furnace. The temperature within the furnace is then increasingly ramped at 15° F. per minute, and the cones are manually observed to detect changes in shape. The fusibility of the ash is recorded at four temperatures; namely, (1) the temperature at which the apex of the cone becomes rounded known as initial deformation temperature (IDT, hereinafter abbreviated as IT); (2) the temperature at which the height of the deformed cone is equal to the width of the base known as the softening temperature (ST); (3) the temperature at which the height of the deformed cone is equal to one-half the width of the base known as the hemispherical temperature (HT); and, finally, (4) the temperature at which the cone has been reduced to a lump having a height no greater than one-sixteenth inch known as the fluid temperature (FT).

This test method has several significant drawbacks. First the method is time-consuming and requires an observer to constantly monitor all cones within the furnace as all cones pass through all four stages of fusion. This task is tedious and the observer can become inattentive, resulting in inaccurate temperature readings. Second, monitoring the shape of five cones (the typical furnace load) is difficult. Third, the findings are somewhat subject to the individual judgment of the human observer, further introducing error and/or variation into the test results. The ASTM test method recognizes these problems and provides for relatively large acceptable errors in excess of 50° C. or 100° F. for each of the four stages of fusion.

Improvements in ash fusion determinators have greatly improved the accuracy of the determination of IT, ST, HT, and FT. An ash fusion determinator Model No. AF700, commercially available from Leco Corporation of St. Joseph, Mich., represents state-of-the-art advances over several earlier determinators, such as disclosed in U.S. Pat. Nos. 4,462,963 and 4,522,787. The AF700 ash fusibility determinator automatically monitors ash cone deformation temperatures in coal ash, coke ash, and mold powders. Prepared ash cones are mounted on a ceramic tray and placed into a high-temperature, rampable furnace. The user selects an analytical method with a predefined furnace atmosphere (oxidizing or reducing) and a ramp rate (° C./minute) for the furnace based on approved methodologies. The furnace is first purged with nitrogen before the selected atmosphere is introduced. A high-resolution digital camera collects images (up to 30 frames/minute) after the furnace temperature reaches the method-defined starting point (typically 1382° F./750° C.). Predefined ash fusibility temperatures (IT, ST, HT, and FT) may be automatically determined using Image Recognition Functions (IRF) within the software. In addition, IRF allows the analysis to be automatically terminated after all deformation points have been reached for all samples, increasing throughput and furnace lifetime. Alternately, the furnace can be programmed to cycle between the method-defined starting temperature (e.g. 752° F./400° C.) and a maximum programmed furnace temperature (typically 2730° F./1500° C. and a maximum of 2900° F./1600° C.). A complete image history for all analyzed samples is digitally archived for easy retrieval and review on DVD, CDRW, or hard drive. Archived images may be used to make subjective determinations of deformation temperatures.

Although such a determinator has greatly improved the efficiency of the determination of the ash fusion temperature, subjective, somewhat error-prone steps, are still required. Although the softening temperature (ST) and hemispherical temperature (HT) phases are well defined in mathematical terms, the initial deformation temperature (IDT or IT) and the fluid temperature (FT) phases remain subjective observations and are much more difficult to accurately determine. Thus, there remains a need for improvement in the accurate determination of the ASTM ash fusion temperatures.

SUMMARY OF THE INVENTION

It has been discovered through extensive testing of coal and coke materials at numerous laboratories utilizing several samples that an algorithm for predicting the IT and FT based upon measured ST and HT temperatures results in more accurate determination of these endpoint temperatures than the actual subjective determination of them. Utilizing multi-linear regression coefficient analytical techniques, the following equations were developed utilizing the empirically gathered data:

For reducing atmospheres:

$$IT = C_1 \times ST - C_2 \times HT + C_3$$

$$FT = C_4 \times HT - C_5 \times ST + C_6$$

For oxidizing atmospheres:

$$IT = C_7 \times ST - C_8 \times HT + C_9$$

$$FT = C_{10} \times HT - C_{11} \times ST + C_{12}$$

Where:
   IT is the initial deformation temperature;
   ST is the softening temperature;
   HT is the hemispherical temperature;
   FT is the fluid temperature; and
   $C_1$-$C_{12}$ are constants determined by multi-linear regression coefficient analytical techniques on the collection of data.

In a preferred embodiment, the constants $C_1$-$C_{12}$ were about (all temperatures are in ° C.):

| | | | |
|---|---|---|---|
| $C_1$ = 1.56 | $C_4$ = 1.87 | $C_7$ = 1.50 | $C_{10}$ = 1.81 |
| $C_2$ = 0.67 | $C_5$ = 0.96 | $C_8$ = 0.57 | $C_{11}$ = 0.89 |
| $C_3$ = 117.71 | $C_6$ = 126.79 | $C_9$ = 77.32 | $C_{12}$ = 122.29 |

In a most preferred embodiment, the constants $C_1$-$C_{12}$ were (all temperatures are in ° C.):

| | | | |
|---|---|---|---|
| $C_1$ = 1.5627 | $C_4$ = 1.8744 | $C_7$ = 1.5016 | $C_{10}$ = 1.8131 |
| $C_2$ = 0.6684 | $C_5$ = 0.9568 | $C_8$ = 0.5724 | $C_{11}$ = 0.8940 |
| $C_3$ = 117.7088 | $C_6$ = 126.7877 | $C_9$ = 77.3248 | $C_{12}$ = 122.2880 |

When Fahrenheit degrees are employed, $C_3$=215.259; $C_6$=230.856; $C_9$=130.665; and $C_{12}$=223.750. All other constants remain the same. With the system and method of the present invention, therefore, an operator of a commercial coal-burning furnace can accurately and relatively quickly determine all of the ash fusion temperatures necessary for the efficient operation of the furnace without the need for extensive and time-consuming burning of coal samples through the FT stage since only the ST and HT stages need to be determined by the ash fusion analyzer.

These and other features, objects and advantages of the present invention will become apparent upon reading the following description thereof together with reference to the accompanying drawings.

BRIEF DESCRIPTION OF THE DRAWINGS

FIG. 2 is a table of one set of collected data for reducing atmospheres for numerous samples determining the IT and FT temperatures;

FIG. 3 is a table of one set of collected data on numerous samples run in oxidizing atmospheres determining the IT and FT temperatures;

FIG. 4 is a set of equations developed empirically from the multi-linear regression process shown in FIG. 1 and collected data, such as shown in FIGS. 2 and 3.

DETAILED DESCRIPTION OF THE PREFERRED EMBODIMENT

Figure 1:
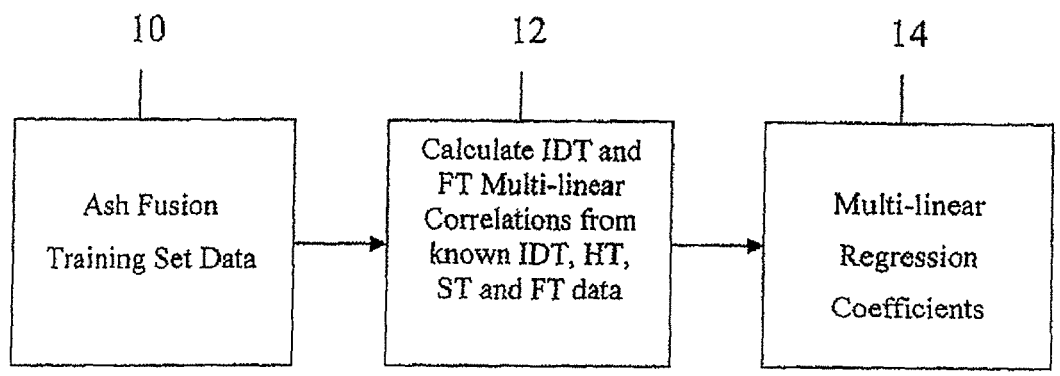
FIG. 1 is a flow diagram showing the process by which the algorithm is developed for calculating the IT and FT temperatures based upon measured HT and ST temperatures.

It has been discovered through extensive testing of coal and coke materials at numerous laboratories utilizing several samples, such as illustrated by the exemplary data shown in FIGS. 2 and 3, that the use of an algorithm for predicting the IT and FT is more accurate than the actual subjective determination of these temperatures utilizing an ash fusion instrument. The data, such as represented in FIGS. 2 and 3, is entered in a computer as indicated by block 10 in FIG. 1. It is understood that data from hundreds of samples was used to develop the ash fusion equations of FIG. 4 and the data of FIGS. 2 and 3 is a sampling of such collected data. As shown by block 12, utilizing conventional multi-linear correlation programs, the IT and FT can be calculated from known IT, HT, ST, and FT data actually determined from measurements, as shown by the examples in the tables of FIGS. 2 and 3. The tables of FIGS. 2 and 3 represent one lab's analysis of multiple samples in reducing and oxidizing atmospheres respectively, it being understood that the training set data entered in block 10 of FIG. 1 is data from over 20 such labs, each of which independently analyzed over 35 coal and coke ash samples to obtain a universe of data which accurately reflects the characteristics of coal and coke samples. Predicted initial deformation IT and fluid FT temperatures using the developed ash fusion equations of FIG. 4 differ from the measured values by an average of 7.51° C. to 16.2° C. These are values much less than the normal errors experienced in determining these two fusion temperatures. By comparison, the average "within lab" errors reported in the measurement of the initial deformation and fluid temperatures of a coal ash ranged from 13.9° C. to 32.9° C.

Utilizing conventional multi-linear regression coefficient analytical techniques, as shown by the process of block 14 in FIG. 1, the ash fusion equations of FIG. 4 were determined utilizing the empirically gathered data (such as shown in FIGS. 2 and 3). The mathematical analysis is also known as the least square method for developing equations to fit data to a plot. One discussion of this time honored technique is discussed in an article entitled "Least Squares," by Hervé Abdi, published in Lewis-Beck M., Bryman, A., Futing T. (Eds.) (2003) *Encyclopedia of Social Sciences Research Methods*, Thousand Oaks (CA), the disclosure of which is incorporated herein by reference. Using this mathematical analysis of the collected data, the series of equations developed for predicting the initial deformation and fluid temperatures were determined and are set forth in FIG. 4. (All temperatures are in C.) If Fahrenheit degrees are employed, the constants $C_3$, $C_6$, $C_9$, and $C_{12}$ change as seen in FIG. 4.

Figure 5:
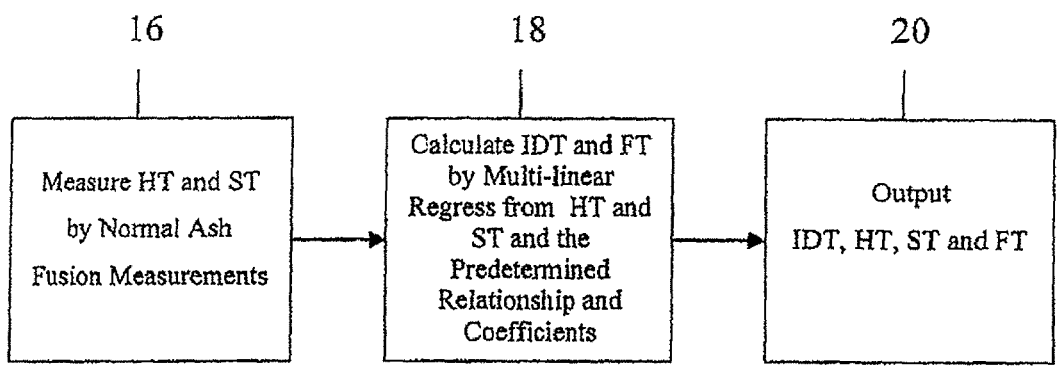
FIG. 5 is a flow diagram of the application of the algorithm to measured HT and ST to determine IT and FT.

When it is desired to determine the ash fusion parameters IT, ST, HT, and FT of a sample for use in coal fired furnaces, as shown in FIG. 5, the first step 16 is to utilize an ash fusion instrument, such as an AF700 available from Leco Corporation of St. Joseph, Mich., for determining only the ST and HT temperatures which, as discussed above, can accurately be determined utilizing existing ash fusion analyzers.

Next, as indicated by block 18 of FIG. 5, employing the data determined from the ash fusion analyzer for ST and HT and utilizing the equations of FIG. 4, an algorithm, programmed into a computer associated with the ash fusion analyzer executes the equations of FIG. 4, to determine the predicted IT and FT from the accurately measured ST and HT. Subsequently, the output information from the computer is supplied to a monitor, printer, or other output device, as shown by block 20, to display both the measured ST and HT from the ash fusion analyzer, as well as the predicted IT and FT based upon application of the formulas of FIG. 4. The output can be in other usable electronic formats.

With the system and method of the present invention, therefore, an operator of a commercial coal-burning furnace can accurately and relatively quickly determine all of the ash fusion temperatures necessary for the efficient operation of the furnace without the need for extensive and time-consuming burning of coal samples through the FT stage since only the ST and HT stages need to be determined by the ash fusion analyzer. Additionally, the exact shape of the specimen being analyzed need not be a conventional cone-shape inasmuch as the ST and HT geometric configurations are well defined and can be determined from a geometric shape other than the classic pyramidal shape of the ASTM standard. Thus, the analytical process described herein is independent of the choice of shape or quality of the sample block employed for the analysis.

It will become apparent to those skilled in the art that various modifications to the preferred embodiment of the invention, including modifications of the mathematical formulas, as described herein can be made without departing from the spirit or scope of the invention as defined by the appended claims.

The invention claimed is:

1. A method of predicting IT and FT values from measured ST and HT temperatures of a specimen by applying a multi-linear regression analysis to measured ST and HT temperatures utilizing a microprocessor, wherein IT and FT values from measured ST and HT temperatures of a specimen are computed by a computer programmed to apply the following formulae:

For reducing atmospheres:

$$IT = C_1 \times ST - C_2 \times HT + C_3$$

$$FT = C_4 \times HT - C_5 \times ST + C_6$$

For oxidizing atmospheres:

$$IT = C_7 \times ST - C_8 \times HT + C_9$$

$$FT = C_{10} \times HT - C_{11} \times ST + C_{12}$$

Where:
IT is the initial deformation temperature;
ST is the softening temperature;
HT is the hemispherical temperature;
FT is the fluid temperature; and
$C_1$-$C_{12}$ are constants determined by multi-linear regression coefficient analytical techniques on the collection of data.

2. The method of claim 1 where $C_1$ is about 1.56, $C_2$ is about 0.67, $C_3$ is about 117.71, $C_4$ is about 1.87, $C_5$ is about 0.96, $C_6$ is about 126.79, $C_7$ is about 1.50, $C_8$ is about 0.57, $C_9$ is about 77.32, $C_{10}$ is about 1.81, $C_{11}$ is about 0.89, and $C_{12}$ is about 122.29 and where the measured temperatures are in °C.

3. The method of claim 1 where $C_1$ is 1.5627, $C_2$ is about 0.6684, $C_3$ is about 117.7088, $C_4$ is about 1.8744, $C_5$ is about 0.9568, $C_6$ is about 126.7877, $C_7$ is about 1.5016, $C_8$ is about 0.5724, $C_9$ is about 77.3248, $C_{10}$ is about 1.8131, $C_{11}$ is about 0.8940, and $C_{12}$ is about 122.2880 and where the measured temperatures are in °C.

4. The method of claim 1 where $C_1$ is 1.5627, $C_2$ is about 0.6684, $C_3$ is about 125.259, $C_4$ is about 1.8744, $C_5$ is about 0.9568, $C_6$ is about 230.856, $C_7$ is about 1.5016, $C_8$ is about 0.5724, $C_9$ is about 130.665, $C_{10}$ is about 1.8131, $C_{11}$ is about 0.8940, and $C_{12}$ is about 223.750 and where the measured temperatures are in °F.

5. A system for the determination of IT, ST, HT, and FT temperatures of a specimen comprising:
an ash fusion analyzer for the determination of ST and HT temperatures;
a computer coupled to said ash fusion analyzer for receiving the ST and HT information therefrom and programmed for performing a multi-linear regression analysis on the ST and HT information for calculating the IT and FT temperatures, wherein said computer is programmed for calculating the IT and FT temperatures based upon the following equations:

For reducing atmospheres:

$$IT = C_1 \times ST - C_2 \times HT + C_3$$

$$FT = C_4 \times HT - C_5 \times ST + C_6$$

For oxidizing atmospheres:

$$IT = C_7 \times ST - C_8 \times HT + C_9$$

$$FT = C_{10} \times HT - C_{11} \times ST + C_{12}$$

Where:
IT is the initial deformation temperature;
ST is the softening temperature;
HT is the hemispherical temperature;
FT is the fluid temperature; and
$C_1$-$C_{12}$ are constants determined by multi-linear regression coefficient analytical techniques on the collection of data.

6. The system as defined in claim 5 where $C_1$ is about 1.56, $C_2$ is about 0.67, $C_3$ is about 117.71, $C_4$ is about 1.87, CS is about 0.96, $C_6$ is about 126.79, $C_7$ is about 1.50, $C_8$ is about 0.57, $C_9$ is about 77.32, $C_{10}$ is about 1.81, $C_{11}$ is about 0.89, and $C_{12}$ is about 122.29 and where the measured temperatures are in °C.

7. The system as defined in claim 5 where $C_1$ is 1.5627, $C_2$ is about 0.6684, $C_3$ is about 117.7088, $C_4$ is about 1.8744, $C_5$ is about 0.9568, $C_6$ is about 126.7877, $C_7$ is about 1.5016, $C_8$ is about 0.5724, $C_9$ is about 77.3248, $C_{10}$ is about 1.8131, $C_{11}$ is about 0.8940, and $C_{12}$ is about 122.2880 and where the measured temperatures are in °C.

8. The system as defined in claim 5 where $C_1$ is 1.5627, $C_2$ is about 0.6684, $C_3$ is about 215.259, $C_4$ is about 1.8744, CS is about 0.9568, $C_6$ is about 230.856, $C_7$ is about 1.5016, $C_8$ is about 0.5724, $C_9$ is about 130.665, $C_{10}$ is about 1.8131, $C_{11}$ is about 0.8940, and $C_{12}$ is about 223.750 and where the measured temperatures are in °F.

9. The system as defined in claim 5 wherein said system includes an output for the values of IT and FT.

10. The system as defined in claim 9 wherein said output is a display.

11. The system as defined in claim 9 wherein said output is a printer

12. A system for the determination of IT, ST, HT, and FT temperatures of a specimen comprising:
a computer for receiving ST and HT data from an ash sample said computer programmed for calculating IT and FT from such information by applying the following equations:

For reducing atmospheres:

$$IT = C_1 \times ST - C_2 \times HT + C_3$$

$$FT = C_4 \times HT - C_5 \times ST + C_6$$

For oxidizing atmospheres:

$$IT = C_7 \times ST - C_8 \times HT + C_9$$

$$FT = C_{10} \times HT - C_{11} \times ST + C_{12}$$

Where:
IT is the initial deformation temperature;
ST is the softening temperature;
HT is the hemispherical temperature;
FT is the fluid temperature; and
$C_1$-$C_{12}$ are constants determined by multi-linear regression coefficient analytical techniques on the collection of data.

13. The system as defined in claim 12 where $C_1$ is about 1.56, $C_2$ is about 0.67, $C_3$ is about 117.71, $C_4$ is about 1.87, $C_5$ is about 0.96, $C_6$ is about 126.79, $C_7$ is about 1.50, $C_8$ is about 0.57, $C_9$ is about 77.32, $C_{10}$ is about 1.81, $C_{11}$ is about 0.89, and $C_{12}$ is about 122.29 and where the measured temperatures are in ° C.

14. The system as defined in claim 12 where $C_1$ is 1.5627, $C_2$ is about 0.6684, $C_3$ is about 117.7088, $C_4$ is about 1.8744, $C_5$ is about 0.9568, $C_6$ is about 126.7877, $C_7$ is about 1.5016, $C_8$ is about 0.5724, $C_9$ is about 77.3248, $C_{10}$ is about 1.8131, $C_{11}$ is about 0.8940, and $C_{12}$ is about 122.2880 and where the measured temperatures are in ° C.

15. The system as defined in claim 12 where $C_1$ is 1.5627, $C_2$ is about 0.6684, $C_3$ is about 215.259, $C_4$ is about 1.8744, $C_5$ is about 0.9568, $C_6$ is about 230.856, $C_7$ is about 1.5016, $C_8$ is about 0.5724, $C_9$ is about 130.665, $C_{10}$ is about 1.8131, $C_{11}$ is about 0.8940, and $C_{12}$ is about 223.750 and where the measured temperatures are in ° F.

16. The system as defined in claim 13 wherein said system includes an output for the values of IT and FT.

17. The system as defined in claim 16 wherein said output is a display.

18. The system as defined in claim 17 wherein said output is a printer.

* * * * *

UNITED STATES PATENT AND TRADEMARK OFFICE
CERTIFICATE OF CORRECTION

PATENT NO. : 8,126,657 B2
APPLICATION NO. : 12/938543
DATED : February 28, 2012
INVENTOR(S) : John T. Riley It is certified that error appears in the above-identified patent and that said Letters Patent is hereby corrected as shown below:

Column 6, claim 6, line 19, "CS" should be --$C_5$--; and

Column 6, claim 8, line 31, "CS" should be --$C_5$--.

Signed and Sealed this
Fifteenth Day of May, 2012

David J. Kappos
*Director of the United States Patent and Trademark Office*